United States Patent
Sasaki et al.

(10) Patent No.: US 6,955,912 B2
(45) Date of Patent: Oct. 18, 2005

(54) **PROCESS FOR PRODUCING *TRICHODERMA HARZIANUM* FERM BP-4346**

(75) Inventors: Yasuharu Sasaki, Room 702, Olympiaodorinishi18chomemansion, 1-3, Odorinishi 18-chome, Chuo-ku, Sapporo-shi, Hokkaido 060-0042 (JP); Susumu Sasaki, Hokkaido (JP)

(73) Assignees: Yasuharu Sasaki, Hokkaido (JP); Hokkaido Green Kosan, Incorporated, Hokkaido (JP)

( * ) Notice: Subject to any disclaimer, the term of this patent is extended or adjusted under 35 U.S.C. 154(b) by 0 days.

(21) Appl. No.: 10/868,199

(22) Filed: Jun. 16, 2004

(65) Prior Publication Data

US 2005/0003514 A1 Jan. 6, 2005

Related U.S. Application Data

(63) Continuation of application No. 10/019,394, filed as application No. PCT/JP01/02772 on Mar. 30, 2001, now abandoned.

(30) Foreign Application Priority Data

Mar. 31, 2000 (JP) ......... 2000-98293

(51) Int. Cl.$^7$ .......... C12N 1/00; C12N 1/02; C12N 1/14; C12N 1/18; C12N 1/20

(52) U.S. Cl. .......... 435/256.7; 435/256.8; 435/261; 435/945

(58) Field of Search .......... 435/256.7, 256.8, 435/261, 945

(56) References Cited

U.S. PATENT DOCUMENTS

| 4,837,155 A | 6/1989 | Tabachnik |
| 6,403,362 B1 | 6/2002 | Moriya et al. |

*Primary Examiner*—David M. Naff
*Assistant Examiner*—Deborah K. Ware
(74) *Attorney, Agent, or Firm*—Wenderoth, Lind & Ponack, L.L.P.

(57) ABSTRACT

The present invention is intended to efficiently produce a large amount of chlamydospores of *Trichoderma harzianum* SK-5-5 mycelia. This objective is achieved by chlamydospores characterized by having been obtained by inoculating a culture medium containing glucose, yeast extract and polypepton with *Trichoderma harzianum* SK-5-5 mycelia and culturing the same to thereby obtain chlamydospores containing conidiospores.

1 Claim, 3 Drawing Sheets

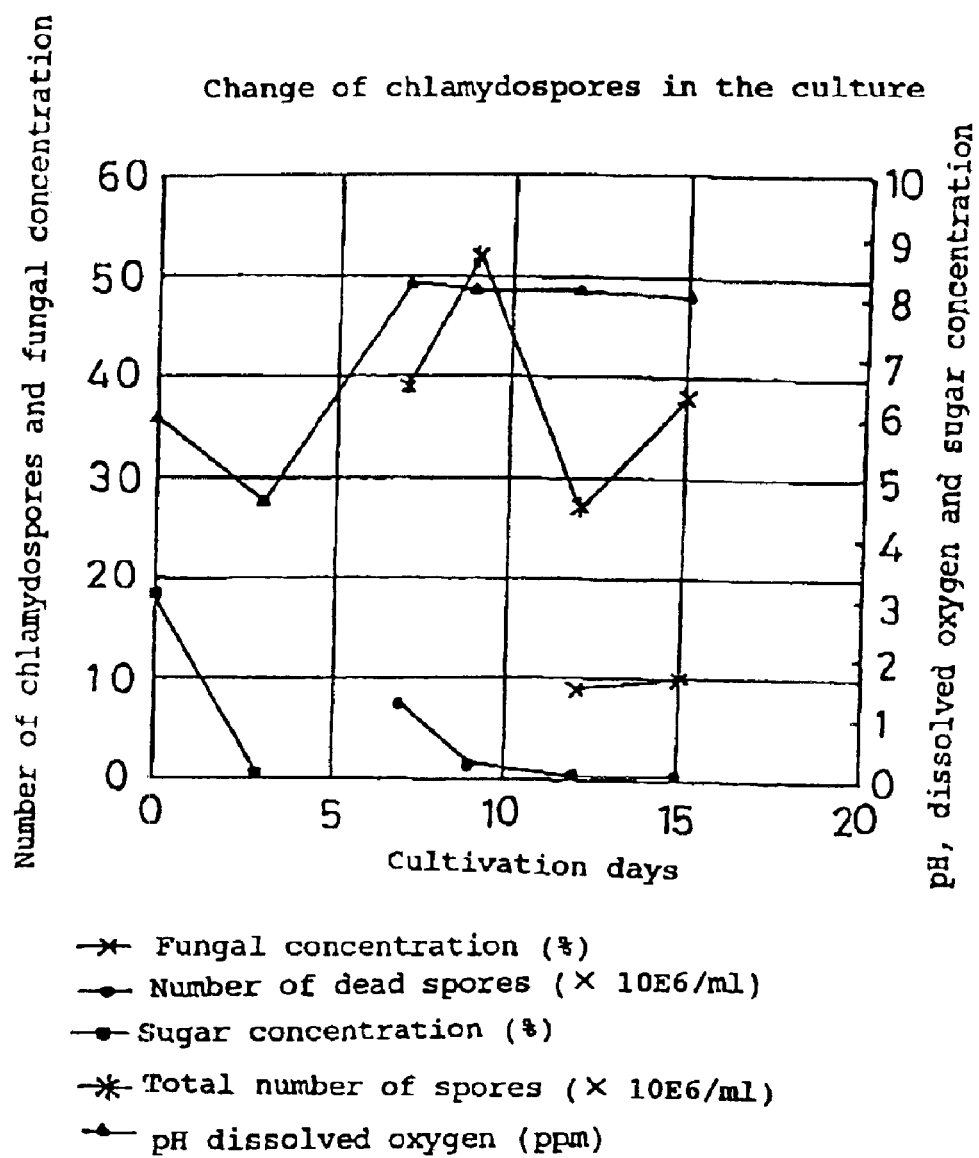

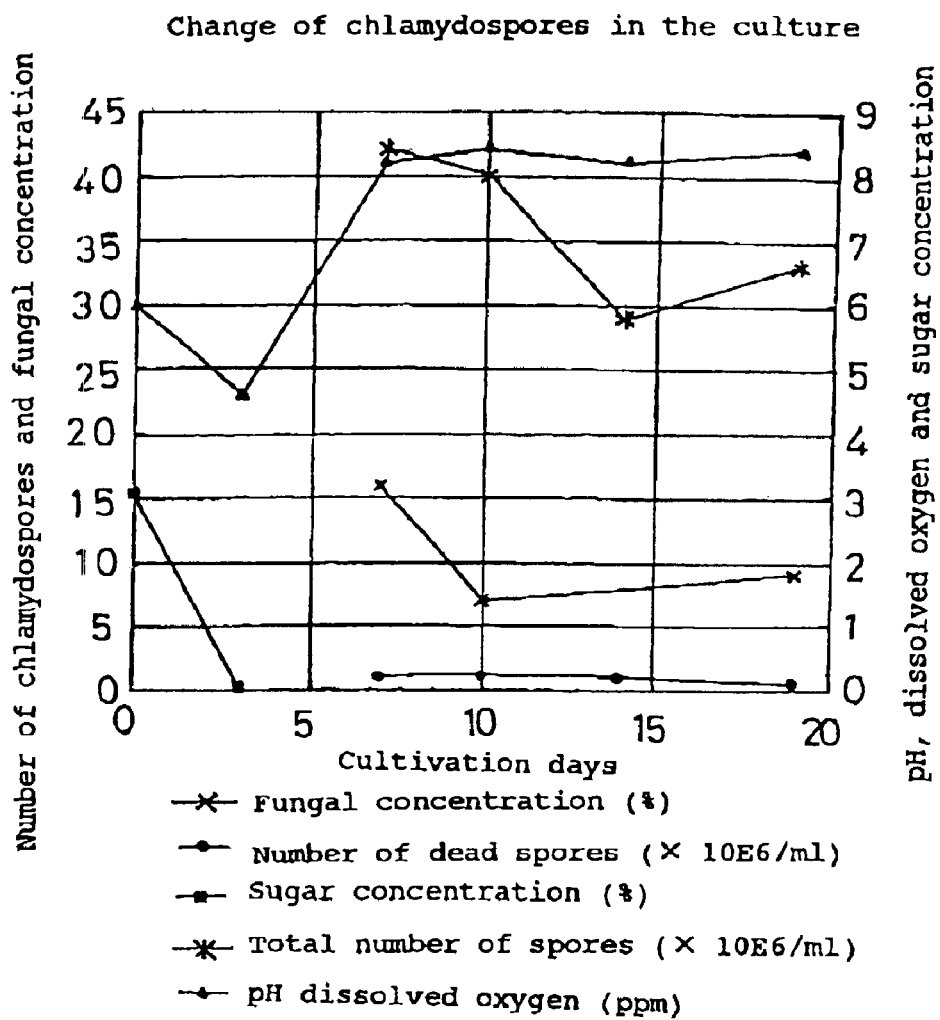

PROCESS FOR PRODUCING *TRICHODERMA HARZIANUM* FERM BP-4346

This is a continuation of Ser. No. 10/019,394, filed Aug. 5, 2002, now abandoned, which is a 371 of PCT/JP01/02772, filed Mar. 30, 2001.

TECHNICAL FIELD

This invention relates to chlamydospores of *Trichoderma harzianum* SK-5-5 and process for producing the same in order to a large quantity of chlamydospores or a mixture of mycocelia, conidiospores and chlamydospores of *Trichoderma harzianum* SK-5-5.

The fungus of *Trichoderma harzianum* SK-5-5 is deposited National Institute of Bioscience and Human-Technology, Agency of Industrial Science and Technology, Ministry of Economy, Trade and Industry of Japan (Address: 1-1-3, Higashi, Tsukuba-shi, Ibaraki, Japan) (Seimeiken) under the deposition number "Bikouken Microbial Deposition No. 13327" (Deposited date: Dec. 9, 1992; Depositary: Hokkaido Green Kosan Inc.). The request for transfer of the original deposit to a deposit based on Budapest Treaty was made on Dec. 9, 1992, and the deposit number BP-4346 was given.

BACKGROUND ART

It has been known to contain a very small amount of chlamydospores in the fungal microorganisms. Said chlamydospores have been known to have high environment adaptability and not to become extinct at high temperature as well as low temperature. The invention on the subject of chlamydospores of *Nimbya scirpicola* K-004 (FERM Bp-4448) and inducing medium thereof has been suggested (Japanese unexamined patent-publication No. JP-A-07-303481).

Since the above mentioed chlamydospores in nature exist at an extremely low level, it is very difficult to collect and use them. Also, it has difficult problems in producing a large amount of the chlamydospores of common fungal microorganisms from the medium disclosed said known invention, effectively.

DISCLOSURE OF THE INVENTION

By virtue of the present invention, a large amount of chlamydospores have been successfully produced by culturing *Trichoderma harzianum* SK-5-5 under aerobic conditions and by providing conditions for generating chlamydospores.

Specifically, the present invention is chlamydospores and process of producing the chlamydospores characterized by inoculating a medium of closely resemble for culturing shiitake mushrooms and the like with *Trichoderma harzianum* SK-5-5 mycelia, culturing the same under aerobic conditions with shaking, facilitating chlamydospore formation by augmenting external stimulus at the time of nutrients consumption, and then separating formed mycelia, conidiospores and chlamydospores from the medium by using centrifugation or other means.

Said medium of closely resemble for culturing shiitake mushrooms and the like is that a medium containing glucose, yeast extract and polypepton as base components, being supplemented with required grain components (e.g. magnesium sulfate, calcium chloride, etc.). In this case, the medium pH is unadjusted.

Above cultivation may be carried out as follows. The temperature is at 27 to 29° C., the aeration is 0.3 vvm, the agitation speed after inoculation is 100 to 200 rpm, the inoculation doses is 0.5 to 0.8% and any pH adjustment is not conducted.

Thus, the present invention is chlamydospores characterized by having been obtained by inoculating a culture medium containing glucose, yeast extract and polypepton with *Trichoderma harzianum* SK-5-5 mycelia and culturing the same to thereby obtain chlamydospores containing conidiospores. The culture medium may contain 2.0 to 3.5% by weight glucose, 0.3% by weight yeast extract, 0.3% by weight polypepton, 0.05% by weight magnesium sulfate, 0.05% by weight calcium chloride and 0.001% by weight antifoaming agent.

Then, the present invention of process is that the process for producing chlamydospores which comprises inoculating a culture medium containing glucose, yeast extract and polypepton with *Trichoderma harzianum* SK-5-5 mycelia, propagating the mycelia under the condition of appropriate temperature, aeration and agitation, maintaining aerated cultivation while facilitating sporulation by augmenting the agitation speed and separating formed mycelia, conidiospores and chlamydospores from the culture medium. The appropriate temperature may be 27 to 29° C., the aeration may be 0.3 vvm, the agitation speed after inoculation may be 100 to 200 rpm and the inoculation dose may be 0.7%. Further, the process of producing chlamydospores comprises increasing the agitation speed by 15 to 30% and maintaining the aerated cultivation, after the glucose consumption in the medium.

In the present invention, it does not affect to propagation of mycelia if the medium pH is not adjusted.

In the above-mentioned invention, the range of cultivation temperature 27 to 29° C. is based on the optimal temperature for *Trichoderma harzianum* SK-5-5 mycelia (hereinafter referred to as "SK-5-5") to propagate.

In the above-mentioned invention, centrifugator or press filtration which is conventionally used for isolation of mycelia is utilized, in order to collect mycelia and chlamydospores from culture.

In the present invention, the reason of agitation speed (frequency of shaking) is increased about two days after the beginning of cultivation is that the difficulty of propagation of mycelia is rise and then the formation of chlamydospores is accelerated. We deemed that SK-5-5 mycelia would be converted into chlamydospores for self-defense, if the agitation speed is increased synchronously with depletion of glucose in the medium (two days after the beginning of cultivation), and, in fact, the chlamydosdpore formation was facilitated.

In the above-mentioned invention, the amount of culture may be 100 ml and the aeration may be 0.3 vvm. It is a matter of course that the amount of culture is larger, the more aeration will require.

The present invention provides a large amount of chlamydospores of SK-5-5, which is superior to thermal tolerant and is homogeneous.

The process of the present invention has an advantageous effect that a large amount of chlamydospores of SK-5-5 can be produced.

BRIEF DESCRIPTION OF THE DRAWINGS

FIG. 2 is a graph of the cultivation days and the number of chlamydospores in other Example of the present invention FIG. 3 is a graph of the cultivation days and the number of chlamydospores in another Example of the present invention

BEST MODE FOR CARRYING OUT THE INVENTION

EXAMPLE 1

Figure 1:
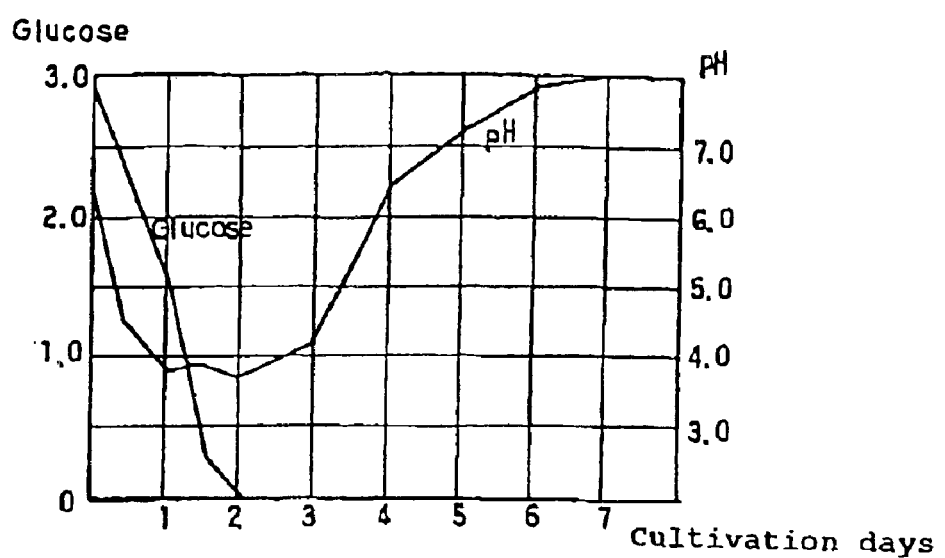
FIG. 1 is a graph of the amount of glucose in the medium during cultivation and the days in the Example of the present invention.

The present invention is explained with reference to an Example.
(1) Seed Cultivation
(Medium)

| | |
|---|---|
| Glucose | 22.0 (g/l) |
| Yeast extract | 3.0 (g/l) |
| Polypepton | 3.0 (g/l) |
| $MgSO_4$ | 0.5 (g/l) |
| $CaCl_2$ | 0.5 (g/l) |
| pH | unadjusted |

100 ml of the medium was poured into a 200 ml conical flask and was inoculated with SK-5-5 (3 g/l). And then the culture was incubated for 7 days under the condition of 28° C., 100 rpm (agitation speed) and 0.3 vvm (aeration volume).

(2) Main Cultivation
(Medium)

| | |
|---|---|
| Glucose | 33.0 (g/l) |
| Yeast extract | 3.0 (g/l) |
| Polypepton | 3.0 (g/l) |
| $MgSO_4$ | 0.5 (g/l) |
| $CaCl_2$ | 0.5 (g/l) |
| Antifoaming agent | 0.1 (g/l) |
| pH | unadjusted |

15 liters of medium was placed in a 30-liter jar. And then 100 ml of seed cultivation obtained in step (1) was added and cultured under the condition of 28° C., 200 rpm (agitation speed) and 0.3 vvm (aeration volume). After the glucose was consumed in the medium (in the day 2 of the cultivation), the formation of sporulation was facilitated by 240 rpm, and the cultivation was maintained for further five days. The cultivation was conducted for seven days under the condition of 28° C., 200 rpm and 0.3 vvm, as described above. The mycelia, conidiospores and chlamydospores were separated from the culture medium by centrifugation.

A drying assistant (e.g. diatomite, zeolite, etc.) was added to the pellet thus separated to the volume of 20 to 30%. The mixture was placed in a reduced pressure desiccator at 30 to 40° C. with stirring until it was dehydrated to 6 to 12% of the water content, and a mixed product of mycelia, conidiospores and chlamydospores was thus obtained.

The mixed product was homogenized aseptically to lyse the mycelia using a homogenizer and then air dried at 50 to 60° C. to obtain a dried preparation.

Additionally, chlamydospores can be isolated from the mixture by centrifugation or any other method and mixed with conidiospores prepared separately at any mixing ratio. In this method, the mixture ratios of chlamydospores and conidiospores are controlled so that various preparations can be provided according to applications, i.e. depending on particular plants or places to which the preparations are applied.

The yields of the conidiospores and chlamydospores were $1.7 \times 10^7$ and $2 \times 10^7$ (CFU/ml), respectively.

In this example, the state of glucose consumption was shown in FIG. 1.

The chlamydospores thus obtained were highly thermal tolerant, and were free from the fear of being disrupted during the storage at temperatures ranging from −5 to +70° C., for example. Moreover, it was demonstrated that thermotolerance of the conidiospores as well as the germination rate of the chlamydospores can be improved when the conidiospores and chlamydospores are packaged in a mixture.

(Exemplary Test) Evaluation of the Resistance of SK-5-5 to Soil Borne Disease

Test microbe: radish *Verticillium dahliae*.

Test plant: radish.

Test drugs: SK-5-5 conidiospore preparation, SK-5-5 clamydospore preparation and bulk powder of SK-5-5 conidiospores.

Control drug: Benlate (SUMITOMO CHEMICAL Co. Ltd.).

Pathogen-bearing soil: infected soil from Hokkaido (provided by Hokkaido Green Kosan Inc.).

Procedure of Inoculation and Disease Development:

150 ml of Sterilized soil was placed in a 250 ml cup (plastic cup), onto which 50 ml of the pathogen-bearing soil was layered. A given dose of each test drug was applied on the surface of the soil (a given volume of the control drug was poured on the soil). Three days after, ten seeds per cup were seeded and then covered with sterilized soil sieved through mesh 8. They were cultivated with usual watering.

Examination Method:

Leaves and stems of radishes were cut off at a position proximal to the covering soil, and the incidence of the disease was determined by examining the browning-blackening of the bundles.

The test was triplicated, and the results are shown in Table 1.

TABLE 1

| | Evaluations | | |
|---|---|---|---|
| | | Items | |
| Test drug | Dose applied | Juveniles developing the disease (%) | Protection effect (%) |
| SK-5-5 conidiospore preparation | 10 g/m² | 52.0 | 27 |
| | 30 g/m² | 61.5 | 14 |
| | 100 g/m² | 22.2 | 69 |
| SK-5-5 chlamydospore preparation | 10 g/m² | 60.9 | 15 |
| | 30 g/m² | 52.4 | 27 |
| | 100 g/m² | 8.8 | 88 |
| SK-5-5 conidiospores (bulk powder) | 10 g/m² | 59.9 | 17 |
| | 30 g/m² | 21.7 | 70 |
| | 100 g/m² | 4.2 | 94 |
| Benlate | | 23.8 | 67 |
| Untreated | | 71.4 | |

Evaluation date: Inoculation with the microbe and treatment with drugs, Nov. 19, 1999; seeding, Nov. 22, 1999; Examination, Jan. 11, 2000.

Results: incidence of the disease was higher in the untreated group. The preparations of conidiospores and chlamydospores showed activity equivalent to that of Benlate at the dose of 100 g/m², although their effects were not verified at the doses of 10 g/m² and 30 g/m².

Furthermore, the bulk powder of the conidiospores showed prominent protection effect at the doses of 30 g/m² and 100 g/m² because of the abundance of the fungi.

EXAMPLE 2

The present invention is explained with reference to another example.

(1) Jar cultivation (medium)

| | | |
|---|---|---|
| Glucose | | 3.3% |
| Polypepton | | 0.3% |
| Magnesium sulfate | | 0.05% |
| Calcium chloride | | 0.05% |
| Antifoaming agent | | 0.01% |
| pH | | unadjusted |
| Seeding volume | | 0.7% |
| Conditions: | Temperature | 28° C. |
| | Agitation speed | 200 rpm |
| | Aeration volume | 0.3 vvm |

The cultivation was conducted for three days under the conditions of aerated liquid culture (with agitation). Three days after, one liter of culture was sampled and 100 ml aliquots of the sample were added to 500 ml conical flasks and cultured for seven days (i.e. cultured for 10 days in total) under the conditions noted below. Results were compared with that obtained from the jar cultivation mentioned above. The results shown in Table 2 were obtained.

TABLE 2

Comparison of cultivation

| Experimental groups | Number of chlamydospores (×10⁷/ml) | Sporulation (%) |
|---|---|---|
| Jar Cultivation | 5.0 | 100 |
| Jar cultivation at 20° C. | 3.5 | 70 |
| Jar cultivation at 35° C. | 1.8 | 36 |
| 1% CACO₃ addition | 2.2 | 44 |
| pH adjusted to 5 | 0.00033 | 0.007 |
| pH adjusted to 9 | 6.0 | 120 |

The only chlamydospores were counted using a Thoma's hemacytometer.

(a) The optimal temperature for sporulation appears to be 28° C. (of the culture).

(b) Different from the current method for spore formation, the effect of the addition of calcium was not observed.

(c) An increased tendency for sporulation was observed at alkaline pH, suggesting the relationship between clamydospore formation and autodigestive enzymes of the fungus.

(d) Sporulation in the medium whose was adjusted pH to 5 was extremely low, which supports for the relationship with autodigestive enzymes.

(e) The spore concentration of $5 \times 10^7$/ml was reproducible, and the sporulation was facilitated by adjusting the pH after depletion of sugar. The concentration of $1 \times 10^8$/ml is likely to be the upper limit of the liquid culture.

(2) The cultivation was conducted under the conditions of 28° C., 200 rpm, 0.3 vvm and 0.2 kg/cm². After 9 days later, the cultivation was conducted at 20° C. and 60 rpm. The results are shown in Table 3.

TABLE 3

Comparison of cultivation

| Cultivation days | PH | Sugar concentration (%) | Dissolved oxygen (ppm) | Fungal concentration (%) | Total number of spores (×10⁷/ml) | Number of dead spores (×10⁷/ml) |
|---|---|---|---|---|---|---|
| 0 | 6 | 3.1 | 8.3 | | | |
| 1 | | | 0 | | | |
| 3 | 4.6 | 0 | 0 | | | |
| 7 | 8.2 | | 8.6 | | 39 | 7.5 |
| 9 | 8.1 | | | | 52 | 1.6 |
| 12 | 8.1 | | 6.1 | 9 | 27 | 0.5 |
| 15 | 8.0 | | 6.3 | 10 | 38 | 0.5 |
| Homogenized treatment | | | 0 | | 550 | 8.0 |

According to the example above, the number of the chlamydospores reached a peak ($4 \times 10^7$/ml) at day 7 after the inoculation, and no increase was observed since then (FIG. 2). The second sample (490 ml) constantly contained 1.0% of dead cells (chlamydospores) after homogenization (at 10,000 rpm for 10 minutes), and such dead cells arisen from homogenization seem negligible. The clamydospore count was measured in the 490 ml of the homogenized culture, and it was $5.5 \times 10^8$/ml.

Since the chlamydospores were found to be effective at the concentration of $5 \times 10^6$/ml, the homogenate may be diluted to 1:100 before use.

(3) The cultivation was conducted under the conditions of 28° C., 200 rpm, 0.3 vvm and 0.2 kg/cm². After 10 days later, the cultivation was conducted at 15° C. and 60 rpm. The results are Table 4.

TABLE 4

Comparison of cultivation

| Cultivation days | PH | Sugar concentration (%) | Dissolved oxygen (ppm) | Fungal concentration (%) | Total number of spores (×10⁷/ml) | Number of dead spores (×10⁷/ml) |
|---|---|---|---|---|---|---|
| 0 | 6 | 3.1 | 5.8 | | | |
| 3 | 4.6 | 0 | 0.5 | | | |
| 7 | 8.2 | | 4.2 | 16 | 42 | 1.0 |
| 10 | 8.4 | | 2.9 | 7 | 40 | 1.1 |
| 14 | 8.2 | | 0 | | 29 | 1.0 |
| 19 | 8.4 | | 0 | 9 | 33 | 0.5 |
| Homogenized treatment | | | 0 | | 190 | 5.4 |

According to the Example above, the number of the chlamydospores reached a peak ($5 \times 10^7$/ml) at day 9 after the inoculation, and no increase was observed since then (FIG. 3). The second sample (490 ml) constantly contained 1.5% of dead cells (chlamydospores) after homogenization (at 10,000 rpm for 10 minutes), and such dead cells arisen from homogenization seem negligible. The clamydospore count was measured in the 490 ml of the homoginized culture, and it was $5.5 \times 10^8$/ml.

Since the chlamydospores were found to be effective at the concentration of $5 \times 10^6$/ml, the homogenate may be diluted to 1:100 before use.

(Example of the Use)

Chlamydospores of *Trichoderma harzianum* SK-5-5 ($5.5 \times 10^8$/ml) diluted to 1:200 were inoculated into sectioned seed tubers by spraying or soaking with 20 ml of the suspension per tuber on average.

The tubers were planted after drying.

When the potatoes were harvested, ten plants were randomly selected from each of the conventional and clamydospore plots to be weighed. The results are shown in Table 5.

TABLE 5

| | Results | | | | |
|---|---|---|---|---|---|
| | S-3L | | 2S or smaller | | Total weight |
| Plot | Number | Weight (g) | Number | Weight (g) | (g) |
| Conventional Plot | 56 | 7,290 | 17 | 360 | 7,650 |

TABLE 5-continued

| | Results | | | | |
|---|---|---|---|---|---|
| | S-3L | | 2S or smaller | | Total weight |
| Plot | Number | Weight (g) | Number | Weight (g) | (g) |
| Clamydospore Plot | 72 | 8,370 | 39 | 1,130 | 9,500 |

As shown in the table, the rate of increased yield was 124%. In this practice, yield is expected to be improved if the tubers are dried more thoroughly after inoculation or treatment with withering agent is put off for 7 to 10 days. This is due to yielding the tubers on the same day despite the retardation of the initial growth.

What is claimed is:

1. A process for producing chlamydospores which comprises inoculating a culture medium containing 2.0 to 3.5% by weight glucose, 0.3% by weight yeast extract, 0.3% by weight polypepton, 0.05% by weight magnesium sulfate, 0.05% by weight calcium chloride and 0.001% by weight antifoaming agent with *Trichoderma harzianum* SK-5-5 (FERM BP-4346) mycelia, the inoculation dose being 0.5 to 0.8% and pH adjustment being not conducted, propagating the mycelia at 27 to 29° C., 0.3 vvm aeration per 100 ml of the culture medium, and at an agitation speed after inoculation of 100 to 200 rpm, maintaining aerated cultivation while facilitating sporulation by augmenting the agitation speed by 15 to 30% after glucose consumption in the medium, and separating formed mycelia, conidiospores and chlamydospores from the culture medium.

* * * * *